(12) United States Patent
Mohr et al.

(10) Patent No.: US 9,260,689 B2
(45) Date of Patent: Feb. 16, 2016

(54) DEVICE FOR A PHOTOCHEMICAL PROCESS

(75) Inventors: Martin Mohr, Hainburg (AT); Franz Emminger, Hainburg (AT)

(73) Assignee: ECODUNA AG, Bruck an der Leitha (AT)

( * ) Notice: Subject to any disclaimer, the term of this patent is extended or adjusted under 35 U.S.C. 154(b) by 295 days.

(21) Appl. No.: 13/254,678

(22) PCT Filed: Mar. 8, 2010

(86) PCT No.: PCT/AT2010/000068
§ 371 (c)(1),
(2), (4) Date: Sep. 2, 2011

(87) PCT Pub. No.: WO2010/102316
PCT Pub. Date: Sep. 16, 2010

(65) Prior Publication Data
US 2012/0003734 A1    Jan. 5, 2012

(30) Foreign Application Priority Data

Mar. 12, 2009 (AT) .................................... 404/2009

(51) Int. Cl.
C12M 1/00 (2006.01)
C12M 1/12 (2006.01)
C12M 1/02 (2006.01)

(52) U.S. Cl.
CPC ............... *C12M 31/08* (2013.01); *C12M 21/02* (2013.01); *C12M 23/06* (2013.01); *C12M 23/22* (2013.01); *C12M 27/00* (2013.01); *C12M 41/10* (2013.01)

(58) Field of Classification Search
CPC ....... C12M 21/02; C12M 23/06; C12M 23/22
USPC ..................................................... 435/292.1
See application file for complete search history.

(56) References Cited

U.S. PATENT DOCUMENTS 3,184,395 A    5/1965 Brewer
3,468,057 A    9/1969 Buisson
(Continued)

FOREIGN PATENT DOCUMENTS

DE    29 51 700    7/1980
DE    41 39 134    6/1992
(Continued)

OTHER PUBLICATIONS

Florian Graetz, "Teilautomatische Generierung von Stromlauf—und Fluidplaenen fuer mechatronische Systeme" 2006.
(Continued)

*Primary Examiner* — Nathan Bowers
*Assistant Examiner* — Gautam Prakash
(74) *Attorney, Agent, or Firm* — Greenblum & Bernstein, P.L.C.

(57) ABSTRACT

Device for a photochemical process includes a reactor. A reaction medium is contained in the reactor and is guided in the reactor in a meandering manner. At least one reactor element is arranged in the reactor through which the reaction medium flows. A light-conducting liquid is utilized. The at least one reactor element comprises one of pipes connected at a bottom and being arranged vertically, pipes connected at a bottom and being inclined at an angle relative to a vertical plane, chambers connected at a bottom and being arranged vertically, and chambers connected at a bottom and being inclined at an angle relative to a vertical plane. The reaction medium is introduced into the reactor and removed therefrom over an upper reaction medium surface and without pressure and freely to the atmosphere such that the flow of the reaction medium is stress-free for micro-organisms disposed therein.

19 Claims, 11 Drawing Sheets

(56) References Cited

U.S. PATENT DOCUMENTS

Figure 9:
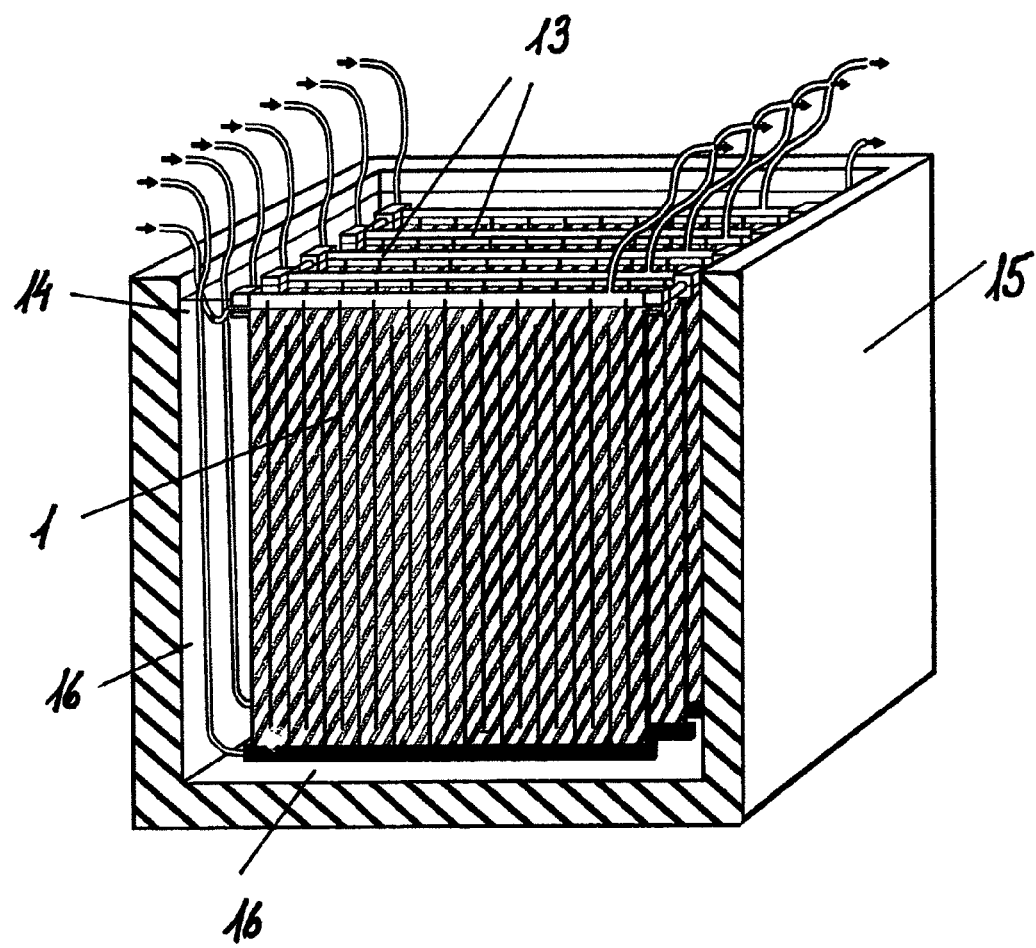

| | | | |
|---|---|---|---|
| 3,768,200 A | 10/1973 | Klock | |
| 5,091,315 A | 2/1992 | McCarty | |
| 5,500,112 A | 3/1996 | McDonald | |
| 6,174,720 B1 | 1/2001 | Oxley | |
| 8,033,047 B2 | 10/2011 | Rasmussen | |
| 8,198,076 B2 * | 6/2012 | Hu et al. | 435/292.1 |
| 2008/0160591 A1 | 7/2008 | Willson et al. | |
| 2008/0274494 A1 | 11/2008 | Kertz | |
| 2008/0293132 A1 | 11/2008 | Goldman et al. | |
| 2009/0130704 A1 | 5/2009 | Gyure | |
| 2010/0330652 A1 | 12/2010 | Mohr | |

FOREIGN PATENT DOCUMENTS

| | | |
|---|---|---|
| DE | 41 34 813 | 4/1993 |
| DE | 195 07 149 | 9/1995 |
| DE | 196 11 855 | 8/1997 |
| DE | 196 44 992 | 3/1998 |
| DE | 197 47 994 | 1/1999 |
| DE | 101 64 458 | 10/2003 |
| EP | 0 738 686 | 10/1996 |
| GB | 2 235 210 | 2/1991 |
| GB | 2 330 589 | 4/1999 |
| JP | 62220183 | 9/1987 |
| WO | 98/18903 | 5/1998 |
| WO | 99/15620 | 4/1999 |
| WO | 2004/074423 | 9/2004 |
| WO | 2008/079724 | 7/2008 |

OTHER PUBLICATIONS

Office Action issued in U.S. Appl. No. 12/865,270 on Mar. 28, 2014 which application is also assigned to Assignee Ecoduna.

* cited by examiner

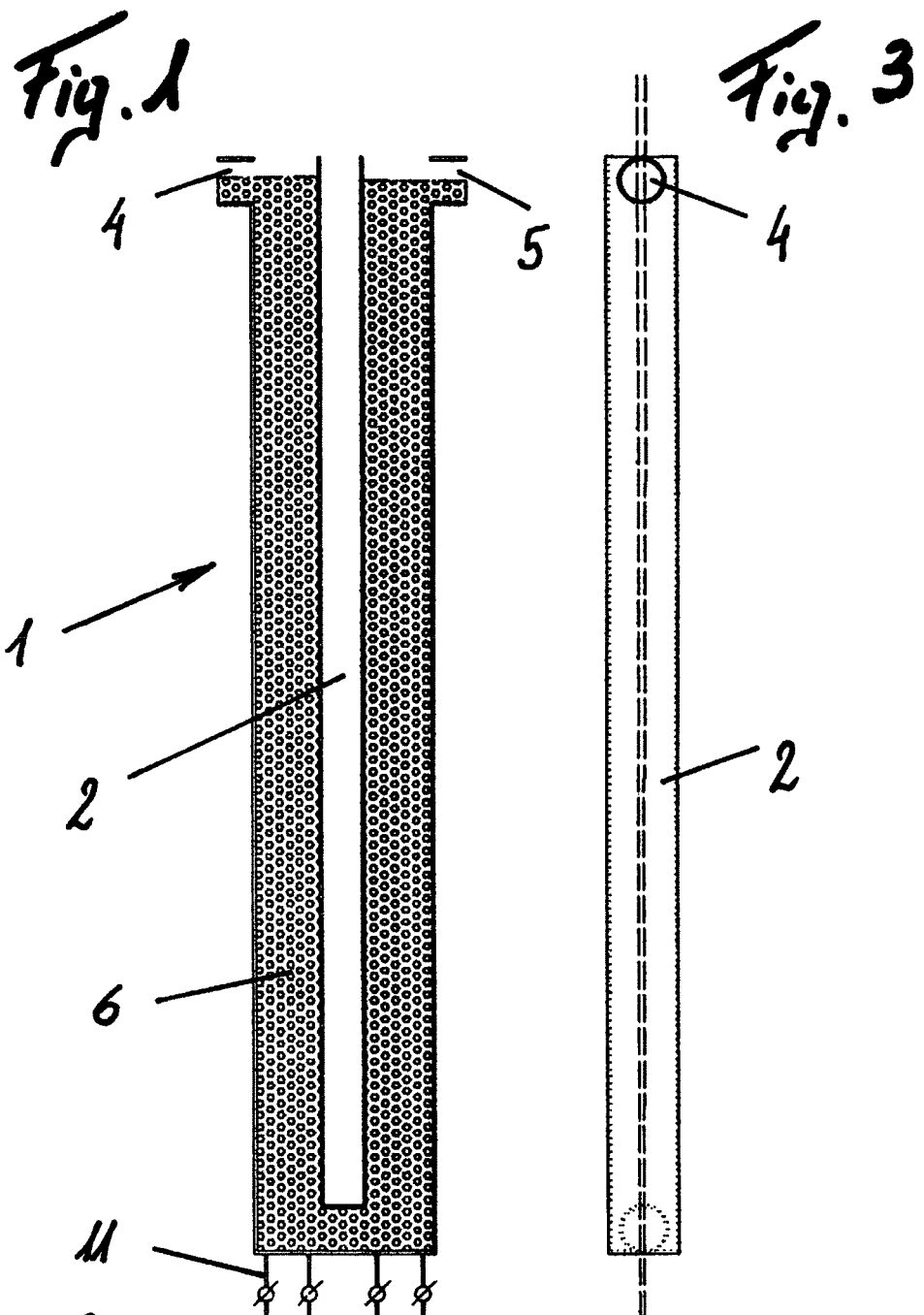
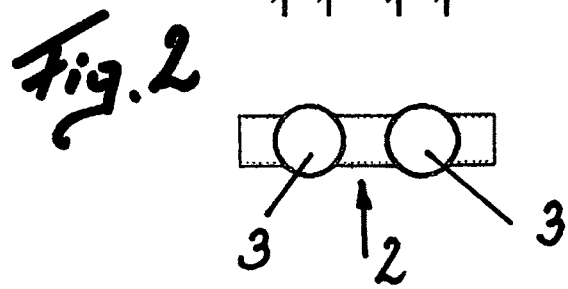

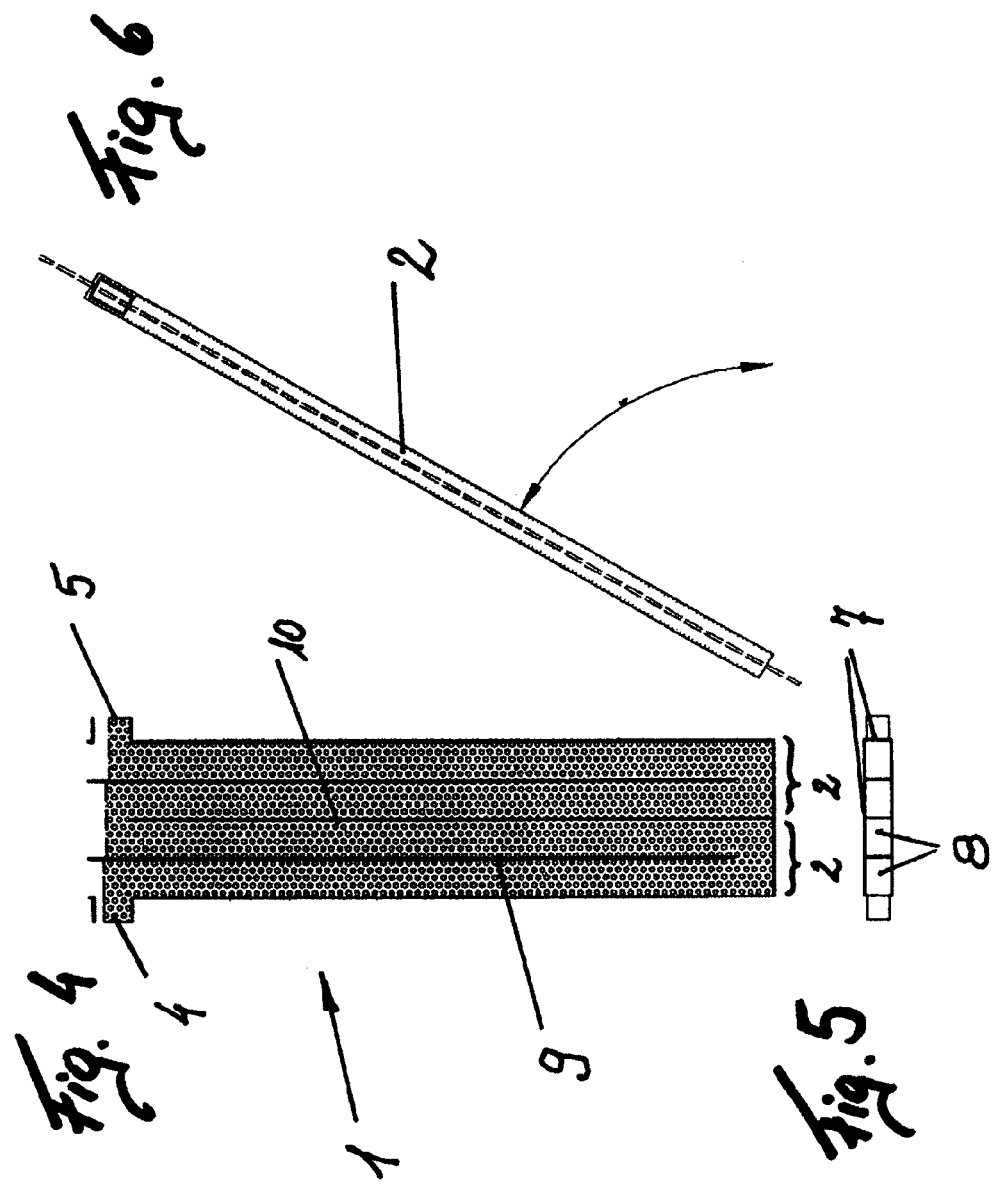

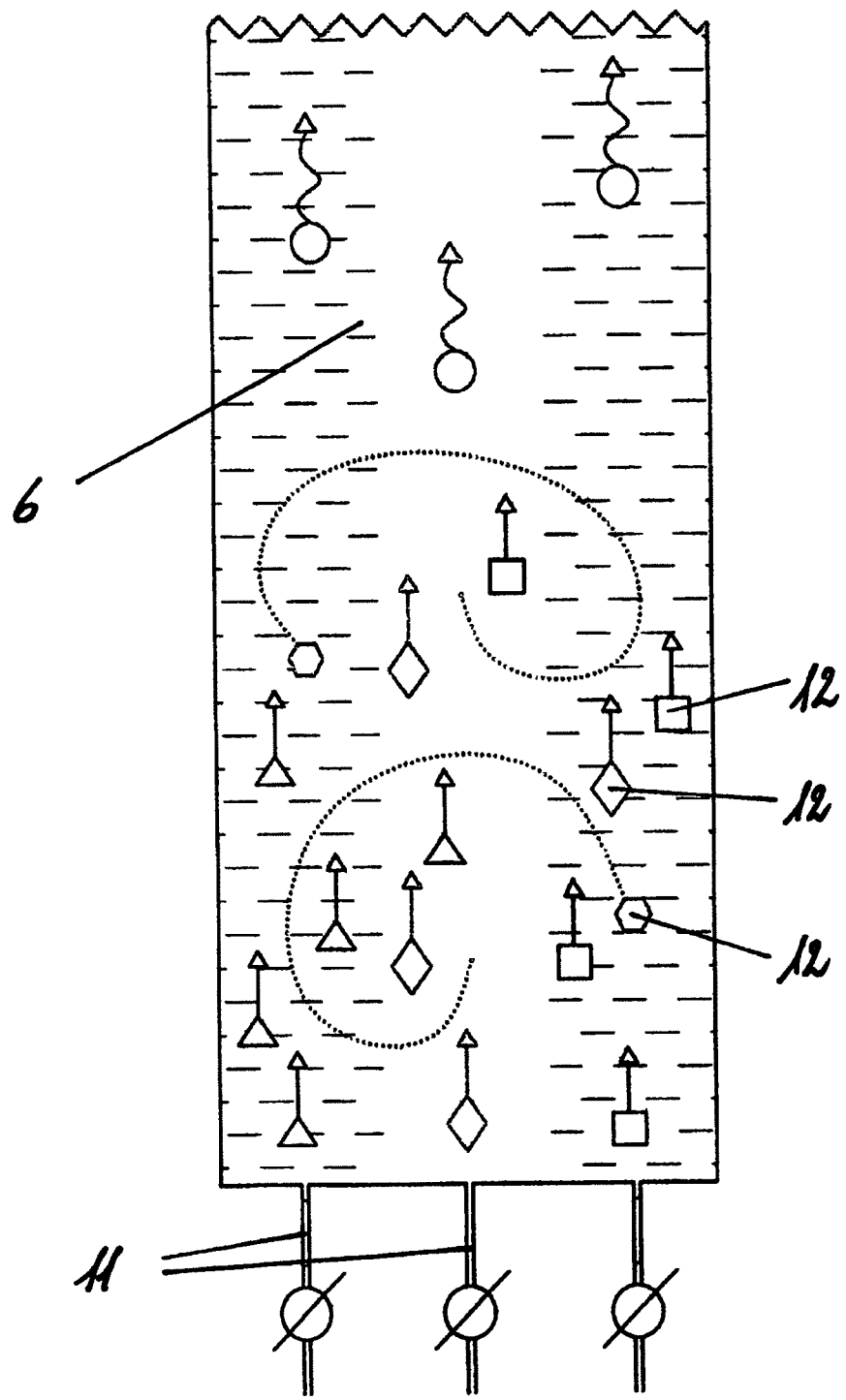

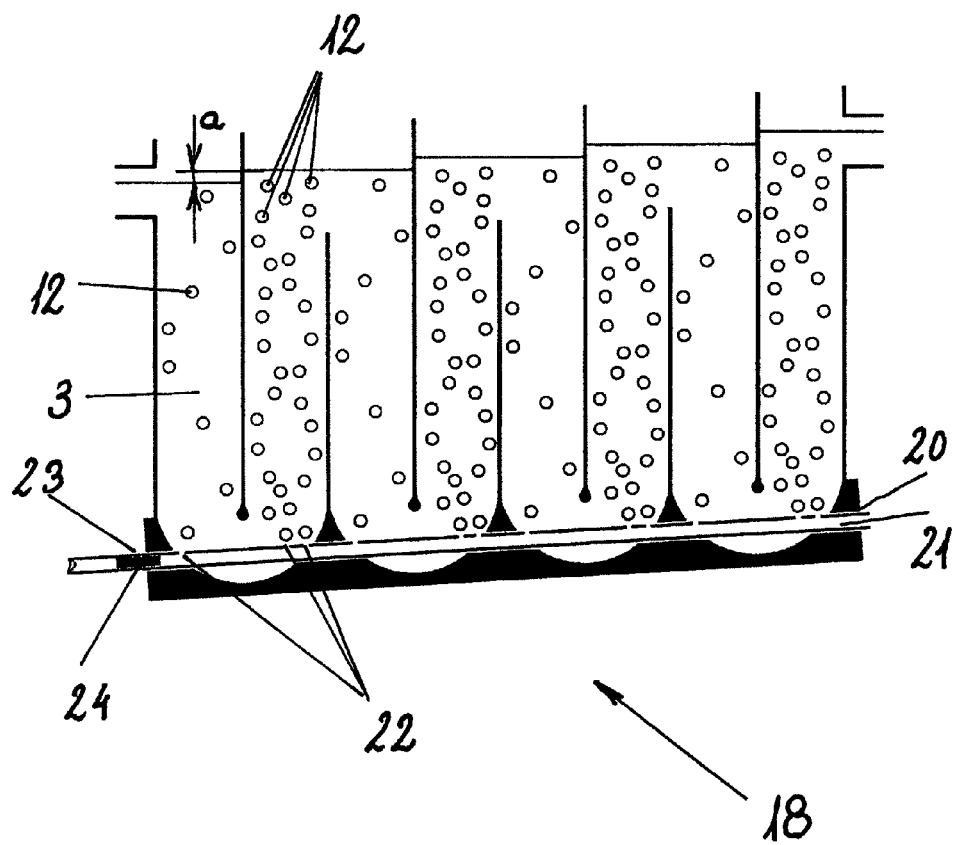

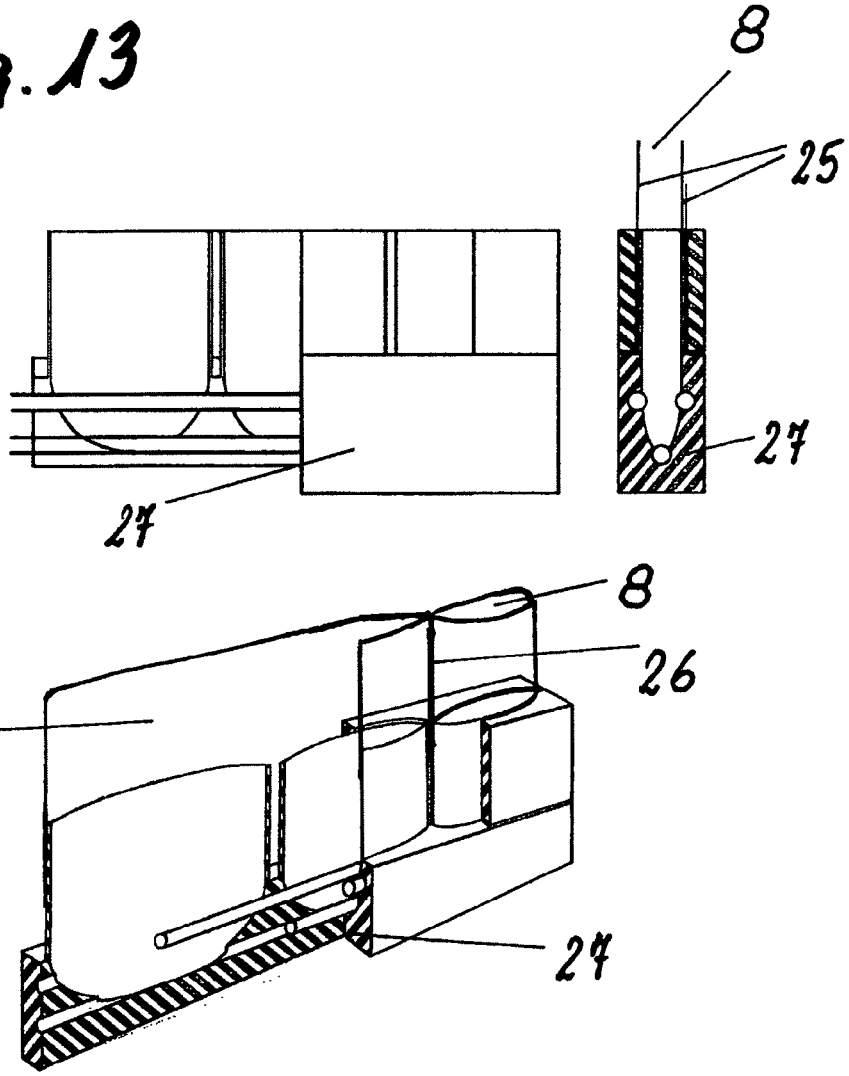

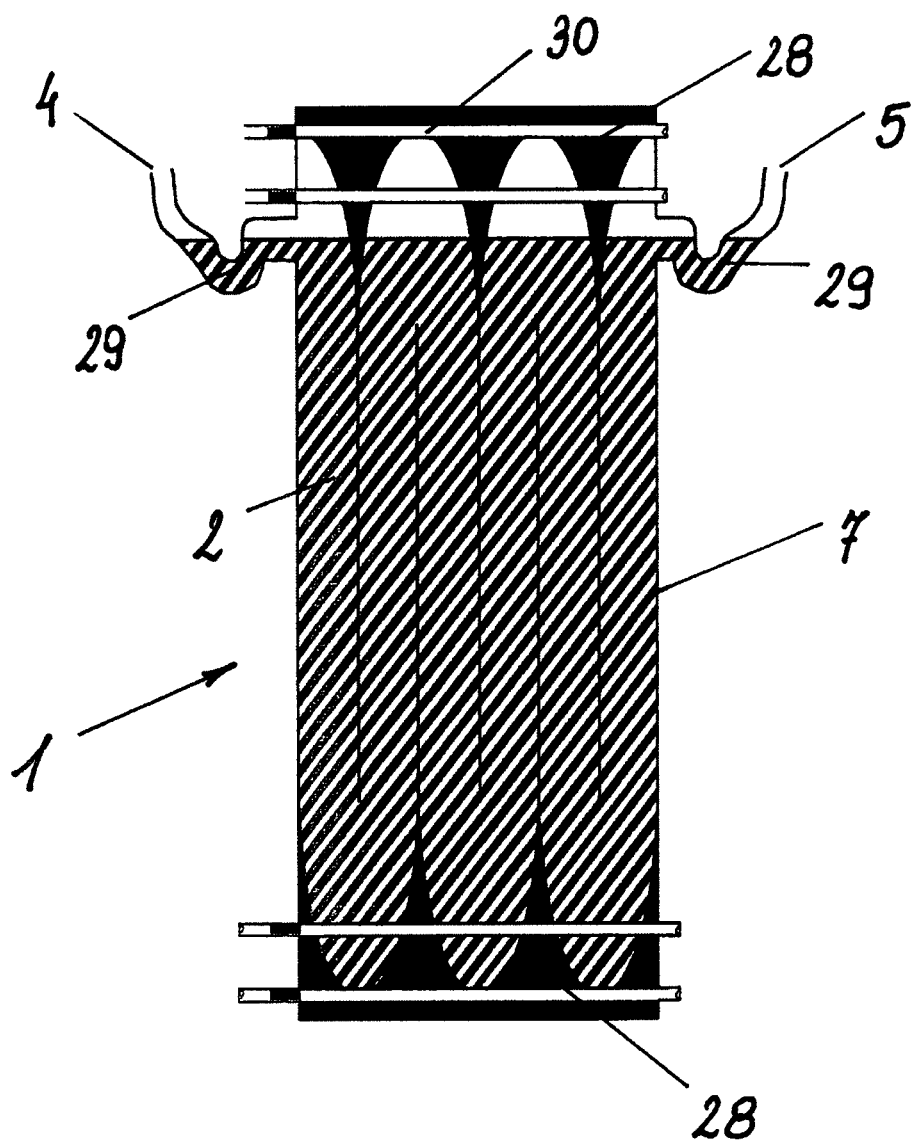

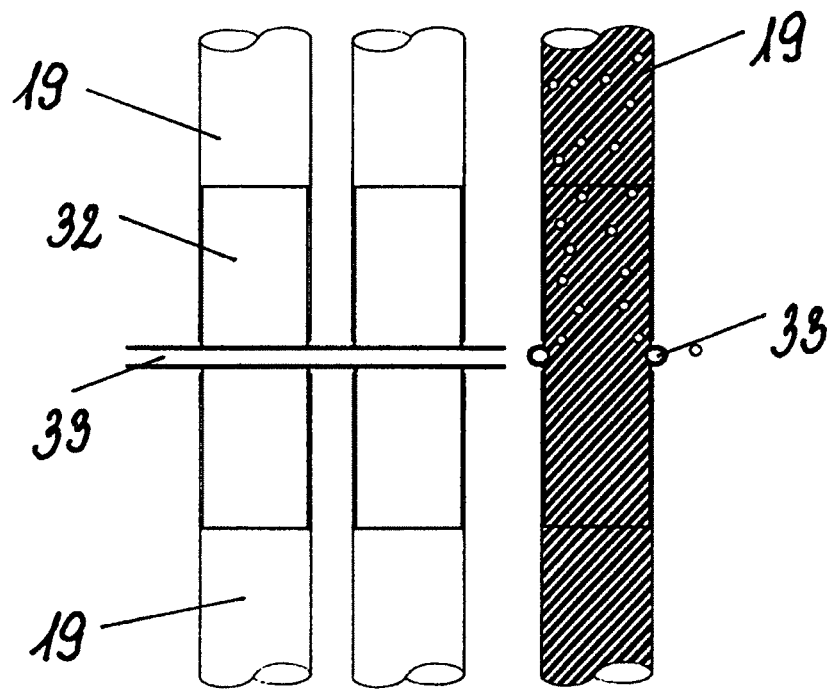
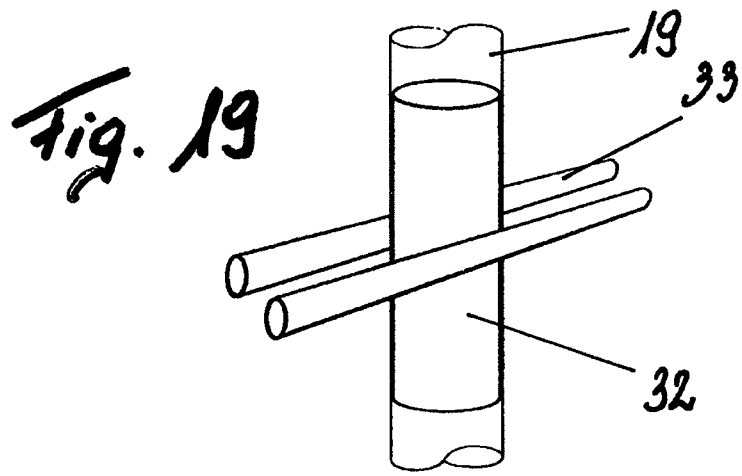

DEVICE FOR A PHOTOCHEMICAL PROCESS

CROSS-REFERENCE TO RELATED APPLICATIONS

The present application is a U.S. National Stage of International Patent Application No. PCT/AT2010/000068 filed Mar. 8, 2010 which published as WO 2010/102316 on Sep. 16, 2010, and claims priority of Austrian Patent Application No. A 404/2009 filed Mar. 12, 2009.

BACKGROUND OF THE INVENTION

1. Field of the Invention

The invention relates to a device for a photochemical process, such as a photocatalytic and/or a photosynthetic process, especially for the cultivation and production or hydrocultivation of preferably phototrophic micro-organisms, wherein a reactor, especially a bioreactor, is provided, and a reaction medium, for example an aqueous solution or a suspension, is guided in the reactor in a meandering manner.

2. Discussion of Background Information

A bioreactor for phototrophic micro-organisms, which is made of glass or plastic, is known from DE 41 34 813 A1. The culture medium is either pumped through the bioreactor or conducted towards the bottom in a meandering manner through the horizontally positioned web plates. In addition, turbulence-creating media are positioned in the webs. In accordance with the method, carbon dioxide is introduced at the top and natural or artificial light is used to operate. The bioreactor is positioned at a right angle to the light source or tracking it.

Furthermore, bioreactors for phototrophic micro-organisms or for photocatalytic processes are also known from GB 2 235 210 A and DE 196 44 992 C1.

Photoctalytic wastewater treatment in a bioreactor is known from EP 738 686 A1, wherein the liquid to be cleaned is conducted through multiple web plates made of transparent plastic. For regulation of the temperature, customary translucent multiple web plates can be used.

Moreover, an actively or passively temperature-controllable solar element made of multiple web plates with at least three belts is described in WO 98/18903. Layers within the reactor are used alternately for a photochemical or photosynthetic process. The culture medium is thereby conducted towards the bottom in a meandering manner in a closed reactor with a sealed front and horizontally positioned web plates.

A bioreactor through which the reaction medium flows horizontally is known from WO 2008/079724 A2, whereby the bioreactor is arranged in a water basin.

Known are of course also the Archimedian screw and the spiral of Da Vinci, for example from Florian Manfred Gratz "Semi-automatic Generation of Circuit and Fluid Diagrams for Mechatronic Systems" (thesis at Munich Tech. Univ. 2006) ISBN 10 3-8316-0643-9.

In addition, a hydropower screw with a trough and a generator for power production is known from DE 195 07 149 C2. A hydropower screw for energy conversion is known from DE 41 39 134 C2.

Naturally, the hydrostatic balance of force is known as hydrostatic paradox, also referred to as Pascal's paradox. This is an apparent paradox which describes the phenomenon that a fluid causes a vertical pressure at the base of a vessel depending on the filling level of the fluid, whereby the shape of the vessel has no influence though.

Vessels which are open at the top and connected at the bottom are called interconnected tanks or interconnected pipes. A homogenous fluid has the same level in these, as the air pressure and gravity have an equal effect on the vessels. In the case of inhomogeneous fluids, the columns of liquid behave inversely to their specific gravity in relation to the level.

Usually, transport in solar reactors is carried out by customary pumping methods, as also in some of the methods mentioned above. This procedure causes stress in the reaction medium, be it due to high pressure, negative pressure, high acceleration or squeezing. Being subjected to this stress, most of the phototrophic micro-organisms relinquish their potential photosynthetic capabilities. Cells are destroyed or damaged and/or the micro-organisms need time and/or metabolic products for regeneration before they can fully recuperate the processes assigned them. Equally, most photochemical processes suffer a drop in their potential photocatalytic capabilities under this stress, as molecules are destroyed or damaged and/or require additional time and/or oxidising agents before they can fully recuperate the processes assigned to them.

SUMMARY OF THE INVENTION

The aim of the invention is to create a device of the type mentioned above, which on the one hand avoids the mentioned disadvantages, and on the other hand, whilst easy and economical to produce due to its method of construction, enables a qualitative and above all quantitative increase in the yield or harvest.

The invention is characterised in that the reactor through which the reaction medium flows includes at least one reactor element comprising two pipes or chambers connected at the bottom that are vertical or inclined at an angle, whereby the reaction medium is both introduced into the reactor and released therefrom, over the upper reaction medium surface, preferably continuously, without pressure and freely to the atmosphere and, as a result of the hydrostatic pressure and level compensation, the flow of the reaction medium is stress-free for the micro-organisms, and that the reactor and its pipes or chambers preferably including a transparent or translucent material are arranged in a light-conducting liquid. With this invention, it is for the first time possible to produce a device for a photochemical process, such as a photocatalytic and/or a photosynthetic process, especially for the cultivation and production or hydrocultivation of preferably phototrophic micro-organisms, which fulfils today's requirements, in particular with regard to quality and operational safety, both in terms of construction costs as well as in operation.

With the device in accordance with the invention and the method underlying the device, it is possible to achieve a gentle transport for the micro-organisms, so that any damage in the course of their production process is prevented. By controlled introduction of the reaction medium in the area of the upper liquid level, the flow rate of the reaction medium through the reactor element can be defined, provided that is filled of course. The reaction medium flows through the perpendicular interconnected reactor elements in a meandering manner. The reactor elements are connected with each other in such a way that the inlet and the outlet are positioned at the top. The reactor elements are completely or partially open towards the top. The flow is achieved by utilisation of the hydrostatic pressure compensation with a minimal loss of height within the entire reactor. Due to the largely pressure-free and appression-free transport of the reaction medium in a biosolar reactor, the reaction process is impaired as little as possible.

In addition, a minimum cost of material is required for the construction of a bioreactor of this type, which increases economic efficiency.

The method and the relevant invention or system in accordance with the invention can be used, by way of example, for the following areas of use:
- photocatalytic clarification of wastewater
- photosynthetic metabolisation of CO2 into oxygen by phototrophic micro-organisms
- cultivation and production of phototrophic micro-organisms for research purposes
- research on photochemical and/or photosynthetic processes
- cultivation and production of phototrophic micro-organisms for food products and basic foodstuff materials
- cultivation and production of phototrophic micro-organisms for basic materials of the pharmaceutical industry
- cultivation and production of phototrophic micro-organisms for fuels and basic materials for fuel production and power generation
- cultivation and production of phototrophic micro-organisms for basic materials of the chemical industry
- cultivation and production of phototrophic micro-organisms which give off exploitable gasses (e.g. hydrogen) within the photosynthetic process.

Stress-free transport of the micro-organisms possibly carried along is quasi enabled by making use of the hydrostatic compensation of forces when the reactor medium flows through the reactor elements. In addition, it is possible to achieve an optimisation of energy, defined conductance of light, an optimisation of space, a supply with additives, defined temperature control, targeted regulation, as well as an improved recovery of gas.

It must also be considered as a significant advantage of the device in accordance with the invention that the temperature of the reaction medium can be controlled through the light-conducting liquid and also through the substances to be introduced into the reaction medium. Furthermore, the device in accordance with the invention has the advantage that the light-conducting liquid acts as a buffer for day-night temperature fluctuations when used in hot regions. As a result, the overall efficiency is increased.

The light-conducting liquid should preferably be as far as possible inanimate to sterile and have the density of seawater where necessary. It is absolutely conceivable that silicone oil may also be used.

In accordance with a special feature of the invention, the dividing wall for a connection of two or more reactor elements into a reactor panel is designed lower than the dividing wall between the pipes or chambers of the reactor element, as a result of which an overflow or interconnected opening is created when the liquid level in the reactor elements is higher than the dividing wall between the reactor elements and the reactor panel can be flowed through in a meandering manner. A reactor element is designed as an interconnected vessel. By this type of serial connection of reactor elements, the option is provided to create a defined flow path.

It is possible to influence the optimal length of stay within the entire reactor in adaptation to the relevant phototrophic micro-organisms or photochemical requirements and in accordance with the process result by the following parameters:
- flow rate
- cross-section of the reactor elements
- height of the reactor elements
- number and condition of non-gaseous substances introduced; condition, number, density and pressure of gasses blown in
- number of reactor elements connected in meander-shaped conductance
- possibility to remove waste-gasses
- process temperatures
- length of stay and position towards light
- length of stay in maturation tanks and/or darkened tanks In an ideal case and if the relevant structural conditions are provided, unique continuous transport of the medium from the inlet to the outlet is possible for the entire process, if necessary.

In accordance with another feature of the invention, the light-conducting liquid surrounding the reactor is provided in a container or basin open at the top, the inner surfaces of which are preferably designed reflecting light. As it is commonly known, light is an absolute prerequisite for any photochemical process, such as a photocatalytic and/or a photosynthetic process. In order to thus provide the biosolar reactor optimally with light, the inner surfaces are designed as reflectors.

In a further embodiment of the invention, reflectors are provided above the light-conducting liquid or above the container or basin, which guide the light, preferably the sunlight, into the light-conducting liquid, preferably at a right angle to the liquid surface. Additional reflectors of this type increase the light optimisation for the process. Due to the vertical introduction of light to the liquid surface and the mirroring of the inner container walls where necessary, the incident light radiation is quasi multiplied, as a result of which the process can be optimised.

In accordance with another embodiment of the invention, light collectors are provided, which are arranged especially before the reflectors, to collect the light that can be guided into the light-conducting liquid. Also in this way, it is possible to achieve an appropriately increased provision with light for the process.

In accordance with a special embodiment of the invention, filters are provided, especially for filtration of the wavelengths that are harmful to the micro-organisms, before the light is guided into the light-conducting liquid. The process can be optimised using relevant filters of this type.

In accordance with another special embodiment of the invention, the light is guided into the light-conducting liquid in a pulsed manner. Depending on the requirements of the process, a pulsed provision with light can also provide even better results.

In accordance with a special feature of the invention, the pipes include foil tubes, especially produced from plastic, the ends of which are connected tightly with diversion devices. These foil tubes have a thin wall thickness and can be procured on the market at a low cost. Due to the pressureless liquid in liquid situation, the foil tubes are not exposed to any forces that could cause possible damage. Since the foil tubes are practically not subjected to any stress as a result, a high lifetime must be expected.

In accordance with an alternative embodiment of the invention, the chambers interconnected in a meander-shaped way are formed by two foils provided with parallel longitudinal welds, whereby the diversion is carried out through diversion devices. The production of a foil welded in this way is also easily possible and inexpensive. Such a foil with a longitudinal weld enables a perpendicular and as far as possible low-resistance flow of a suspension enriched with micro-organisms and nutrients for the cultivation of phototropic micro-organisms.

In accordance with an embodiment of the invention, the diversion device is a U-shaped pipe element with a preferably elliptical cross section, which is connected with the chambers formed by the longitudinal welds. These diversion devices effect an upper and/or lower diversion of the suspension without permitting any contamination of the micro-organisms in the surrounding area. When installed for foil tube reactors, single tubes made of plastic foil are pulled over the ends of the pipes and fastened. For longitudinally welded reactors, the two sides are clamped to elliptical pick-up tubes.

In accordance with a special embodiment of the invention, the preferably prefabricated diversion device is a U-shaped pipe element which comprises at least one borehole for a plug-in pipe or an integrated plug-in pipe comprising micro-boreholes for the introduction of liquid and/or gaseous additives into the reaction medium or for the removal of gaseous process products at the bottom side of the reactor. These lower diversions make it possible to provide the micro-organisms with at least a liquid and/or a gaseous nutrient. Depending on the running process, the introduction can be performed at every diversion or at distances.

In the upper diversion, gasses or other substances accumulating in the process can be removed at the same time as the suspension is diverted without contaminating the suspension with foreign organisms from the surrounding area by using the gas pipes for evacuating excess gasses or gasses created in the process.

In accordance with an advantageous further development of the invention, the plug-in pipe is provided with a larger number of micro-boreholes and/or micro-boreholes with a larger diameter in the area of the reaction medium flowing from the bottom up than in the area of the reaction medium flowing from the top down or in the direction of gravity. This way, and in accordance with the operating process of a mammoth pump, the liquid level in the pipe or chamber passed through from the bottom up is raised in comparison with the pipe or chamber passed through from the top down in a kind of "gas lift effect". The difference in the liquid level can lead to a rise of the liquid level at the end of the last pipe or chamber in comparison with the first pipe or chamber in the case of a multiple serial connection of such units and an increased introduction of gas into each ascending pipe, if the rise of the liquid level is taken into account in the design of the reactor. Despite this increased introduction of preferably gaseous additives, a stress-free transport of the micro-organisms is enabled.

In accordance with an embodiment of the invention, the plug-in pipe is provided with an outer and/or inner thread at both ends. The gas pipes, for example, are designed in such a way that these can close off gastight with the assembly by means of a union nut. At least one of these union nuts is provided with a connection for a gas line.

In addition, the gas pipe can be provided with a connecting piece via its inner thread, which in turn can be screwed onto another gas pipe.

For replacement, the union nut is screwed off at one side, the connecting piece is attached, and the new gas pipe is attached to the other end of the connecting piece. Using the new gas pipe, the gas pipe to be replaced is pushed through the assembly and thereby takes up its position at the same time. This way, it is ensured that the gas pipe to be replaced is pushed through the assembly at a minimal loss of gas or loss of liquid using the new gas pipe. This design permits maintenance or modification of the gas inlet unit without operational interruption or only minimal impairment of the process.

The replacement of the gas pipes can fulfil the following functions within parts of the photobioreactors or the total system:
    for maintenance
    to change the flow rate
    to change the nutrient solution
    to adapt the nutrient solution to the phase of life of the phototropic micro-organisms
    to fight diseases
    to harvest the micro-organisms
    to kill off parts or the totality of micro-organisms In accordance with a special embodiment of the invention, an Archimedian screw or a spiral of Da Vinci or a mammoth pump is provided both inside the reactor as well as between reactors for transport of the reaction medium. In the case of such an arrangement, one or more tubes or webs are rolled up spirally on an axis with single or multiple bearings and mounted robustly using any technical method, such as for example screwed, glued, etc. The relevant tubes or webs are open at both ends. The transport element is aligned and supported in such a way that the bottom end of the tubes or webs scoops reaction medium from a receptacle.

However, tubes or webs are dipped only so far into the reaction medium that the tube end or web emerges above the surface outside of the reaction medium at each rotation.

By slow rotation in the direction of the spiral, which does not result in any significant centrifugal forces, the reaction medium in the relevant lower halves of the tubes or webs is transported to the upper end of the screw via hydrostatic pressure compensation. Upon each rotation, the liquid contained in the top half-turn is released and falls into a receptacle that is positioned at a higher level than the original receptacle. By alternatively full or partial closure of the transport device, spilling and/or an outlet of gas can be prevented.

In accordance with a special feature of the invention, a cover, for example a dome made of transparent or translucent material, such as for example a glass dome, is provided over the container or basin in which the device is provided for a closed construction method of the system. This way, the advantage is provided that it is possible to recover the evaporated liquid as a result of the closed construction method when used in so-called hot regions.

The invention also provides for a device for a photochemical process, wherein the device comprises a reactor, a reaction medium contained in the reactor and being guided in the reactor in a meandering manner, at least one reactor element arranged in the reactor through which the reaction medium flows, and a light-conducting. The at least one reactor element comprises one of pipes connected at a bottom and being arranged vertically, pipes connected at a bottom and being inclined at an angle relative to a vertical plane, chambers connected at a bottom and being arranged vertically, and chambers connected at a bottom and being inclined at an angle relative to a vertical plane. The reaction medium is introduced into the reactor and removed therefrom over an upper reaction medium surface and without pressure and freely to the atmosphere such that the flow of the reaction medium is stress-free for micro-organisms disposed therein.

In embodiments, the photochemical process comprises at least one of a photocatalytic process, a photosynthetic process, a process of cultivation micro-organisms, a process of producing micro-organisms, a hydrocultivation process, and a process for cultivating or producing phototrophic micro-organisms.

In embodiments, the reactor is a bioreactor and the reaction medium is one of an aqueous solution and a suspension.

In embodiments, one of the reactor comprises a transparent material and the reactor comprises a translucent material.

In embodiments, one of said at least one reactor element comprises a transparent material and said at least one reactor element comprises a translucent material.

In embodiments, the at least one reactor element is arranged within the light-conducting liquid.

In embodiments, the at least one reactor element comprises one of two or more reactor elements and a dividing wall connecting the two or more reactor elements, two or more reactor elements arranged in a reactor panel, two or more reactor elements, a dividing wall, and an overflow or interconnected opening arranged above a liquid level in the reactor and two or more reactor elements, a dividing wall, and an overflow or interconnected opening arranged above an upper end of the dividing wall.

In embodiments, one of the light-conducting liquid and the reactor are arranged within one of a container and or basin which is open at a top end and the light-conducting liquid and the reactor are arranged within one of a container and or basin which comprises light reflecting inner surfaces.

In embodiments, the device further comprises one of reflectors arranged above the light-conducting liquid, reflectors arranged above the container or the basin, reflectors structured and arranged to guide light into the light-conducting liquid, reflectors structured and arranged to guide light into the light-conducting liquid at right angle a light-conducting liquid surface, and reflectors structured and arranged to guide sunlight into the light-conducting liquid at right angle a light-conducting liquid surface.

In embodiments, the device further comprising one of light collectors collecting light and guiding the light into the light-conducting liquid, light filtering filters filtering light before it is guided into the light-conducting liquid, and a guiding arrangement structured and arranged to guide light into the light-conducting liquid in a pulsed manner.

In embodiments, the pipes of said at least one reactor element comprise one of foil tubes, plastic tubes, and tubes whose ends are connected with diversion devices.

In embodiments, the chambers of said at least one reactor element comprise connected foils provided with parallel longitudinal welds and diversion devices.

In embodiments, the at least one reactor element comprises one of a U-shaped pipe element connected with chambers formed by a longitudinal weld and a U-shaped pipe element having an elliptical cross section.

In embodiments, the at least one reactor element comprises one of a U-shaped pipe element which comprises at least one borehole, a U-shaped pipe element which comprises a plug-in pipe, a U-shaped pipe element which comprises an integrated plug-in pipe, a U-shaped pipe element which comprises micro-boreholes, a U-shaped element which comprises at least one opening structured and arranged to allow introduction of an additive into the reaction medium, and a U-shaped element which comprises at least one opening structured and arranged to allow removal of gaseous process products at a bottom side of the reactor.

In embodiments, the at least one reactor element comprises first openings structured and arranged to cause a downward flow of the reaction medium in one part of the at least one reactor element and second openings structured and arranged to cause an upward flow of the reaction medium in another part of the at least one reactor element.

In embodiments, the first openings are different in size than the second openings.

In embodiments, the device is adapted to utilize at least one of an Archimedian screw, a spiral of Da Vinci pump, a mammoth pump, a fluid transporter arranged inside the reactor, and a fluid transporter arranged between the reactor and another reactor.

In embodiments, the device is structured and arranged to be used in combination with one of a cover, a dome, a transparent material cover, a translucent material cover, and a cover arranged over a container or basin containing therein the device.

The invention also provides for a bioreactor for a photochemical process, wherein the device comprises at least one reactor element, a reaction medium contained in the reactor element and being guided in the reactor element in a meandering manner, a light-conducting liquid arranged outside the at least one reactor element. The at least one reactor element comprises one of pipes connected at a bottom and being arranged vertically, pipes connected at a bottom and being inclined at an angle relative to a vertical plane, chambers connected at a bottom and being arranged vertically, and chambers connected at a bottom and being inclined at an angle relative to a vertical plane. The reaction medium is introduced into the reactor and removed therefrom over an upper reaction medium surface under atmosphere pressure such that the flow of the reaction medium is stress-free for micro-organisms disposed therein.

The invention also provides for a bio-solar reactor comprising plural reactor elements connected in series, a reaction medium structured and arranged to move through each of the plural reactor elements in a meandering up and down manner and a light-conducting liquid arranged outside the plural reactor elements. Each of the plural reactor elements comprises one of pipes connected at a bottom and being arranged vertically, pipes connected at a bottom and being inclined at an angle relative to a vertical plane, chambers connected at a bottom and being arranged vertically, and chambers connected at a bottom and being inclined at an angle relative to a vertical plane. The reaction medium is introduced into the reactor and removed therefrom under atmosphere pressure such that the flow of the reaction medium within and between the plural reactor elements is stress-free for micro-organisms disposed therein.

DETAILED DESCRIPTION OF THE INVENTION

Figure 10:
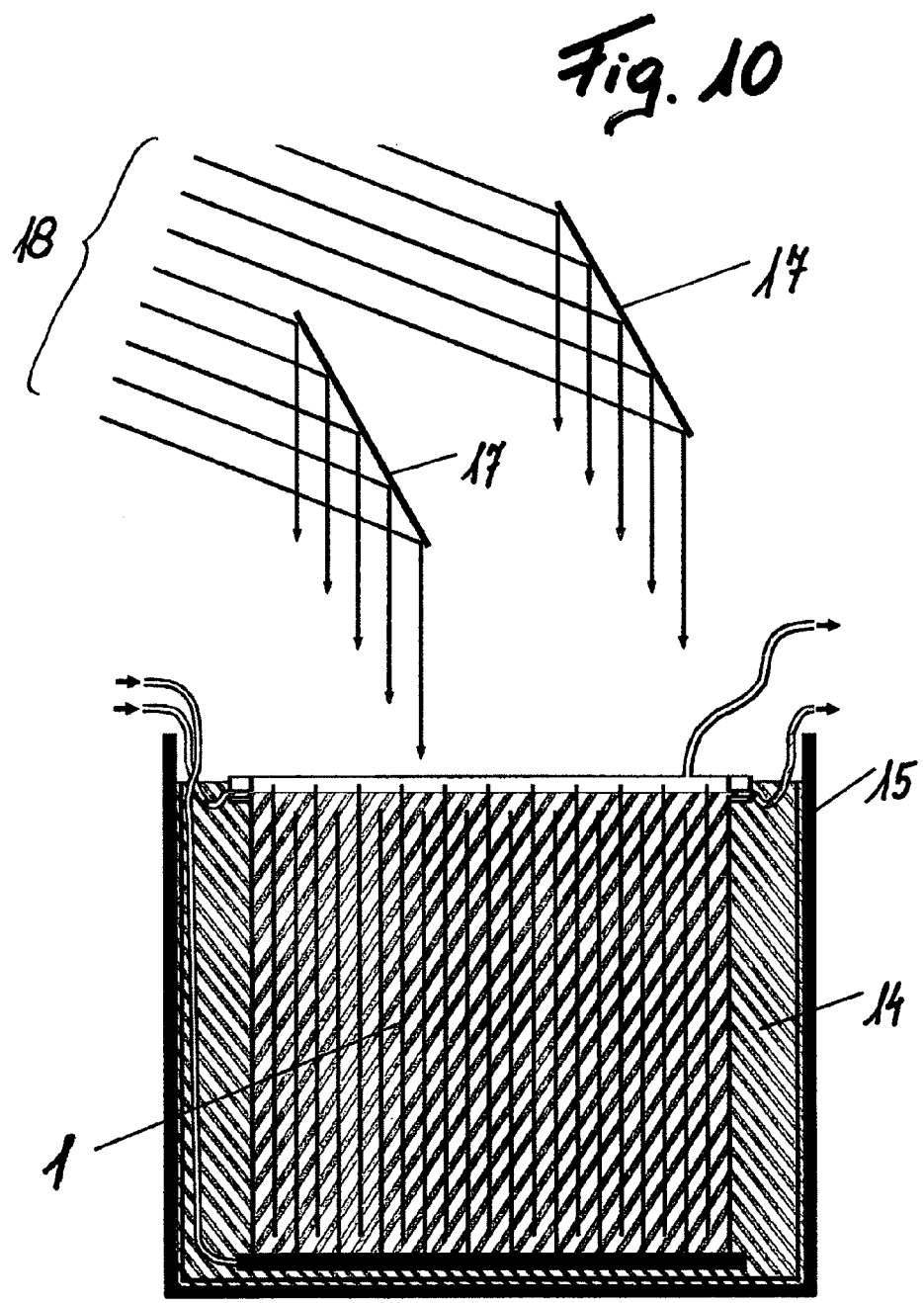
Figure 11:
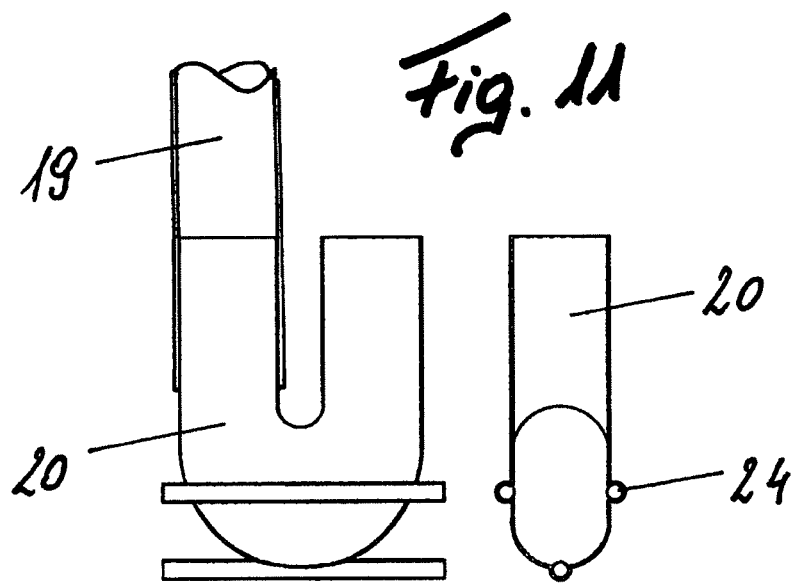
Figure 12:
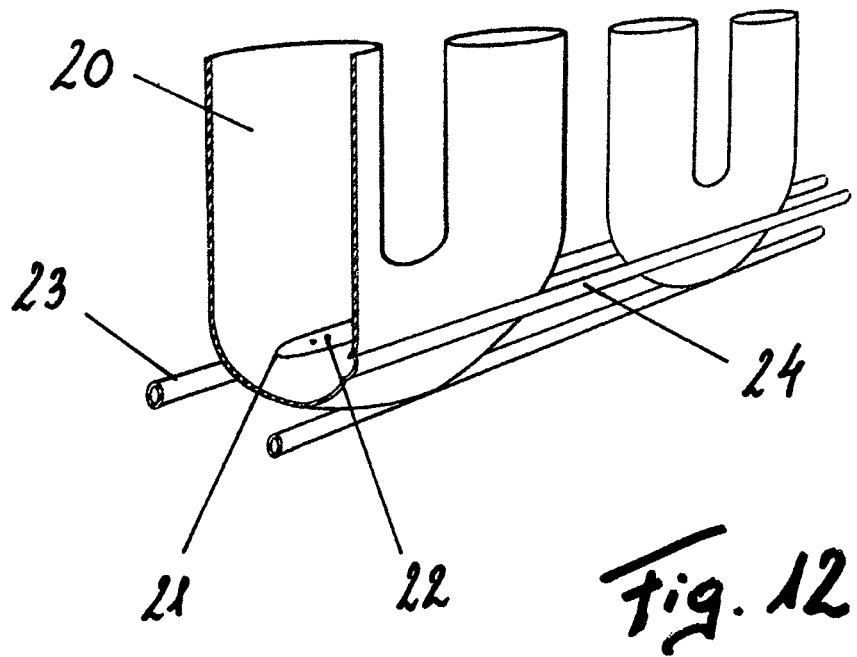
Figure 16:
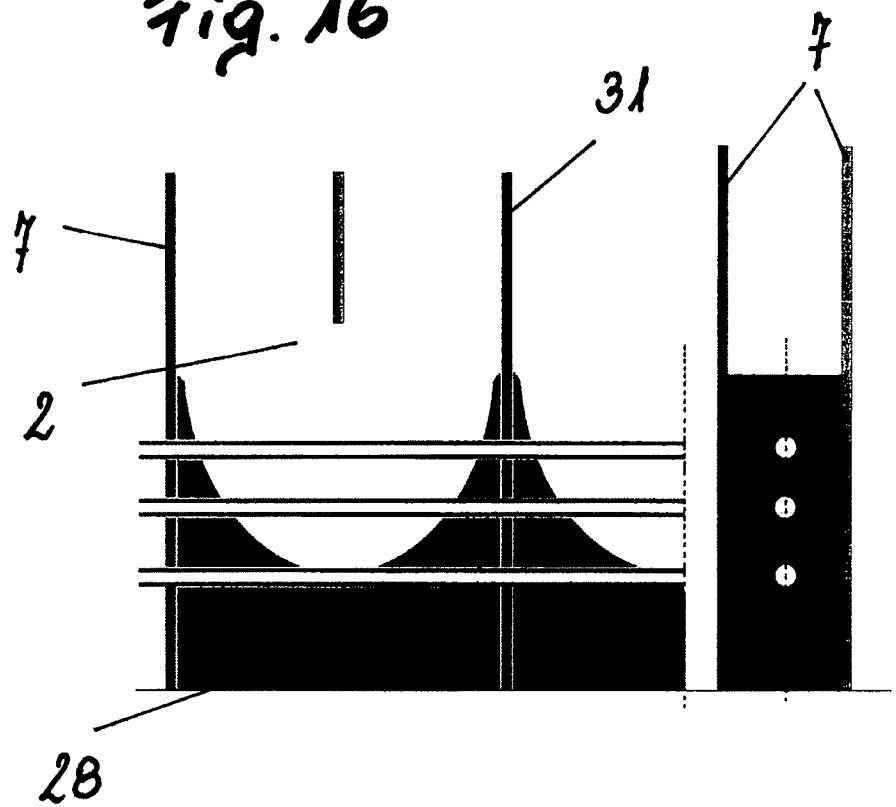
Figure 17:
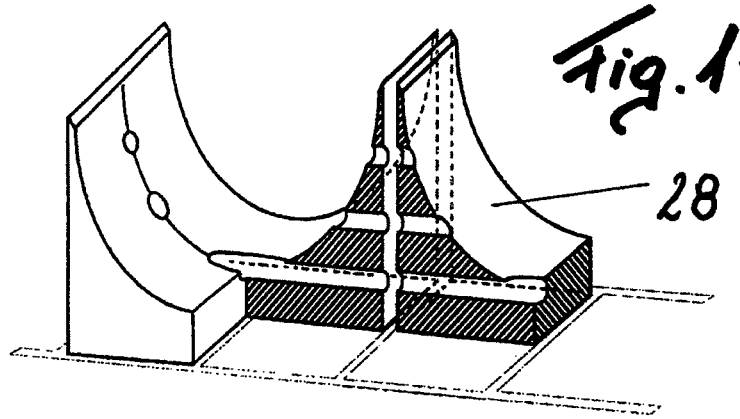

The invention is explained in more detail on the basis of exemplary embodiments illustrated in the figures wherein:

FIG. 1 shows a bioreactor including pipes,
FIG. 2 shows a top view in accordance with FIG. 1,
FIG. 3 shows a side elevation in accordance with FIG. 1,
FIG. 4 shows a bioreactor including of web plates,
FIG. 5 shows a top view in accordance with FIG. 4,
FIG. 6 shows a side elevation in accordance with FIG. 4,
FIG. 7 shows a schematic illustration of a pipe,
FIG. 8 shows a schematic diagram for the "gas lift" effect,
FIG. 9 shows a device for a photochemical process in a basin,
FIG. 10 shows a schematic illustration of the light guidance,
FIG. 11 and FIG. 12 show a diversion device for foil tubes,
FIG. 13 and FIG. 14 show a diversion device for longitudinally welded foils,
FIG. 15 shows a schematic illustration of a device made of multiple web plates,
FIG. 16 and FIG. 17 show a diversion device for the device in accordance with FIG. 15, and FIG. 18 and FIG. 19 show an introduction of additives in the middle part of the foil tubes.

DETAILED DESCRIPTION OF THE INVENTION

In accordance with FIGS. 1 to 3, a reactor, in particular a biosolar reactor 1, comprises at least one reactor element 2, which is formed by two perpendicular pipes 3 connected at the bottom. An inlet 4 and an outlet 5 are provided at the upper reactor edge. For the assembly of a biosolar reactor 1, a multitude of reactor elements 2 are connected in series, whereby an outlet 5 is always connected with an inlet 4.

A biosolar reactor 1 of this type is used for a method for a photochemical process, such as a photocatalytic and/or photosynthetic process, especially for the cultivation and production or hydrocultivation of preferably phototrophic microorganisms. For operation thereof, the biosolar reactor 1 is filled with a reaction medium 6, for example an aqueous solution or a suspension. During operation, the biosolar reactor 1 is only fed via its first inlet 4. The conductance or direction of flow of the reaction medium 6 is carried out upright, preferably perpendicularly, once from the top down and from the bottom up in a reactor element 2. If multiple interconnected reactor elements 2 are connected in series, the reaction medium 6 flows through the reactor in a meandering manner. Both the introduction or feeding as well as the removal of the reaction medium 6 into and/or from the biosolar reactor 1 are preferably carried out continuously, without pressure and freely to the atmosphere via the upper reaction medium surface or closely above the upper liquid level or in the area of the upper liquid level of the reaction medium 6.

The reactor elements 2 are thus connected with each other in a meander-shaped way as interconnected pipes 3, whereby the inlet 4 and the outlet 5 are positioned at the top. The reactor elements 2 are completely or partially open towards the top, depending on need.

Due to the hydrostatic pressure compensation and levelling, a flow of the reaction medium 6 is produced by feeding reaction medium 6 at the inlet 4. For the method, this means that a flow of the reaction medium 6 is produced that is stress-free for the micro-organisms. This way, a free flow is enabled between the individual reactor elements 2 without having to supply any additional energy.

The reaction medium 6 moves through the reactor in a meandering manner with a minimal loss of height in the liquid's effort to compensate the difference in level between the inlet 4 and the outlet 5.

An alternative design for a biosolar reactor 1 is shown in accordance with FIGS. 4 to 6. The biosolar reactor 1 comprises web plates or multiple web plates 7. In the case of the design, a reactor element 2 comprises two preferably rectangular, perpendicular chambers 8 formed by the web plates or multiple web plates 7, which is formed by a dividing wall 9 that is open at the bottom. Both the inlet 4 for introduction or feeding as well as the outlet 5 are provided at the upper reactor edge. Two reactor elements 2 are connected already in the exemplary embodiment shown in accordance with FIG. 4.

If two or more reactor elements 2 are connected, their dividing wall 10 is designed lower than the dividing wall 9 between the pipes 3 or chambers 8 of the reactor element 2. As a result, an overflow or interconnected opening is created when the liquid level in the reactor elements 2 is higher than the dividing wall 10 between the reactor elements 12. This way, the energy consumption is minimised due to the fact that pumps can largely be omitted between the process steps and a random number of equal or different process steps can be coupled with each other at the same flow level.

The individual reactor elements 2 can be designed transparent or translucent, or also light-proof, if required. Both glass or UV-transmittant plastic, such as e.g. polymethylmethacrylate, can be used as materials.

The biosolar reactor 1 is filled and operated in analogy to the designs ad FIGS. 1 to 3.

With regard to incident light radiation onto the reactor elements 2, which is described in more detail later, an inclined reactor is shown in accordance with FIG. 6. Although the reactor is inclined at an angle, the reaction medium 6 flows once from the top down or in the direction of gravity and from the bottom up or against the direction of gravity.

In accordance with FIG. 1 and FIG. 4, at least one introductory inlet 11, for example a controllable valve, is provided at the bottom side of the reactor in the area of the diversion of the reactor medium 6 for continuous or batch-by-batch introduction of additives 12, such as for example nutritive solutions or gasses and/or oxidising agents and/or active substances and/or dissolved substances or gasses promoting the process, preferably performed during the process.

In accordance with the method, the reaction medium 6 is optionally saturated with $CO_2$ or other gasses before entering into the reactor. The degree of saturation is concentrated in accordance with the requirements of the process and/or supplied with $CO_2$ or other gasses during the stay in the reactor. The decreasing level of $CO_2$ in the reaction medium 6 caused by steady growth of the micro-organisms during the photosynthetic process can be compensated by continuous and/or paged introduction of $CO_2$.

The decreasing efficiency in the reaction medium caused by steady reaction during the photochemical process can be compensated by continuous and/or batch-by-batch introduction of additional active gasses.

By introducing the additives at the bottom end of the liquid column via the introductory inlets 11 in accordance with FIG. 7, the additives are mixed thoroughly and distributed equally in the reaction medium 6.

The introduction of additives 12, such as fluids and gasses, also optimises the provision with light, as all molecules or phototrophic micro-organisms are conducted sufficiently to the light-flooded light zone of the reactor element 2 near the outer wall, indicated by the arrows 13, due to the resulting turbulence in the reaction medium 6.

The introduction of fluids and gasses produces turbulence in the reaction medium 6, whereby another advantageous result takes effect, namely that a continuous cleaning of the inner reactor surface is caused by the ascent of the gas bubbles.

Furthermore, the reaction medium 6 can also be heated or cooled by defined introduction of fluids and gasses. The introduced additives 12 can thus be used for controlled temperature regulation of the reaction medium 6.

In accordance with FIG. 8, the liquid and/or gaseous substances or additives 12 are introduced at the bottom side in the area of the diversion of the reaction medium 6. In a special embodiment of the reactor, a larger quantity of liquid and/or gaseous substances or additives 12 is introduced in the area of the reaction medium 6 flowing from the bottom up or against the direction of gravity than in the area of the reaction medium 6 flowing from the top down or in the direction of gravity. This way, as mentioned already and in accordance with the operating process of a mammoth pump, the liquid level in the pipe 3 or chamber passed through from the bottom up is raised in comparison with the pipe 3 or chamber 8 passed through from the top down in a kind of "gas lift effect". The difference in the liquid level a can lead to a rise of the liquid level at the end of the last pipe 3 or chamber 8 in comparison with the first pipe 3 or chamber 8 in the case of a multiple serial connection of reactor elements 2 and an increased introduction of gas into each ascending pipe 3, if the rise of the liquid level is taken into account in the design of the reactor. Despite this increased introduction of preferably gaseous additives 12, a stress-free transport of the micro-organisms is enabled.

In accordance with FIG. 9, the reactor through which the reaction medium 6 flows includes at least one reactor element 2 comprising two pipes 3 or chambers 8 connected at the bottom that are vertical or inclined at an angle. A multitude of these reactor elements 2 are connected in series into a reactor panel 13. The reactor panels 13 preferably connected with each other in series are arranged in a frame-like manner, nearly in parallel to each other and preferably mounted firmly, into a reactor, in particular a biosolar reactor 1. The biosolar reactor 1 with its reactor panels 13 is arranged in a light-conducting liquid 14. The light-conducting liquid 14 can be provided in a basin or a container 15.

The reaction medium 6 is both introduced into the reactor and released therefrom, over the upper reaction medium surface, preferably continuously, without pressure and freely to the atmosphere. As a result of the hydrostatic pressure and level compensation, the flow of the reaction medium 6 is stress-free for the micro-organisms.

In practice, contrary to the illustration in the drawing, the reactor panels 13 are naturally connected in series into a biosolar reactor 1 and the introduction or removal is carried out at one place.

The upper side of the respective reactor panel 13 is provided either with a float or fastened suspended from the top, so that the upper reactor edge cannot immerse below the upper edge of the surrounding liquid and thus a situation that is open at the top is provided.

The bottom side of the reactor panel 13 is designed in such a way that it permits nearly perpendicular suspension in the light-conducting liquid 14 due to the own weight or due to additional weights.

As mentioned already, the provision of light to the surface of the reactor panels 13 of the biosolar reactor 1 is of immense importance. To create this prerequisite, the light-conducting liquid 14 surrounding the reactor is provided in a container 15 or basin open at the top, the inner surfaces 16 of which are preferably designed reflecting light.

Above the container 15 or basin in which the biosolar reactor is provided, a cover, for example a dome made of transparent or translucent material, such as for example a glass dome, can be provided for a closed construction method of the system.

In order to improve the light conditions for the biosolar reactor even further, reflectors 17 are provided above the light-conducting liquid 14 or above the container 15 or basin in accordance with FIG. 10, which guide the light, preferably the sunlight 18, into the light-conducting liquid 14, preferably at a right angle to the liquid surface. To collect the light that can be guided into the light-conducting liquid 14, light collectors (not shown) can be arranged before the reflectors 17. Equally, filters can be provided, especially for filtration of the wavelengths that are harmful to the micro-organisms, before the light is guided into the light-conducting liquid 14. The light can also be guided into the light-conducting liquid 14 in a pulsed manner.

In accordance with FIG. 11 and FIG. 12, the pipes 3 include foil tubes 19, which are produced especially from plastic and with thin walls. The ends of these foil tubes 19 are connected tightly with diversion devices 20. The preferably prefabricated diversion device 20 is a U-shaped pipe element which comprises at least one borehole 21 for a plug-in pipe 23 or an integrated plug-in pipe 24 comprising micro-boreholes 22 for the introduction of liquid and/or gaseous additives 12 into the reaction medium 6 or for the removal of gaseous process products at the bottom side of the reactor.

In accordance with FIG. 13 and FIG. 14, an alternative solution is shown for the formation of a reactor panel 13. The chambers 8 interconnected in a meander-shaped way are formed by two foils 25 provided with parallel longitudinal welds 26. The diversion is carried out through diversion devices 27 again. The diversion device 27 is a U-shaped pipe element with a preferably elliptical cross section, which is connected with the chambers 8 formed by the longitudinal welds.

In accordance with FIG. 15, a biosolar reactor 1 made of a multiple web plate 7 is shown. In the case of this embodiment, the device is designed as compact device, whereby the diversion device 28 is connected tightly with the upper and the lower end of the web plate 7. The reactor can be provided with siphons 29 before the inlet 4 and/or after the outlet 5. As a result, the reaction medium 6 can be fed to the first reactor element 2 pressure-freely or without pressure through the siphon 29. The reactor is provided with the plug-in pipes 23 for introduction of the additives 12 at its bottom side. At its top side, additional plug-in pipes 30 are provided for the removal of gaseous process products, such as for example oxygen, preferably during the process. These plug-in pipes 30 are provided above the reaction medium surface or above the upper side of the reactor elements 2. For the removal of these gaseous process products, a collecting device provided above the liquid level of the reaction medium 6 or above the upper side of the reactor elements can be provided.

In accordance with FIG. 16 and FIG. 17, a diversion device 28 including single parts for a biosolar reactor 1 produced from web plates 7 is shown. Thereby, the individual webs 31 are adapted to the relevant inner shape of the web plate 7. The plug-in pipes 23 for introduction of the additives 12 are integrated.

In accordance with FIG. 18 and FIG. 19, a foil tube 19 is shown, whereby the additives can also be introduced along the height, for example at half-height, of the foil tubes 19. The foil tube 19 can be divided thereby at its half height and a plastic connector 32 be provided to connect both parts. plastic connector 32 has the lines 33 provided with micro-boreholes for introduction of the additives 12.

With regard to the plug-in pipes 23, it must still be mentioned that an outer and/or inner thread is provided at both ends. For replacement, the union nut is screwed off at one side, a connecting piece is attached, and the new gas pipe is attached to the other end of the connecting piece. Using the new gas pipe, the gas pipe to be replaced is pushed through the assembly and thereby takes up its position at the same time. This way, it is ensured that the plug-in pipe 23 to be replaced is pushed through the assembly at a minimal loss of gas or loss of liquid using the new gas pipe 21. This design permits maintenance or modification of the gas inlet unit without operational interruption or only minimal impairment of the process.

For stress-free transport of the reaction medium 6, an Archimedian screw or a spiral of Da Vinci or a mammoth pump can be provided both inside the reactor as well as between reactors.

The invention claimed is:
1. A device for a photochemical process, the device comprising:
    a light conducting liquid arranged in a vessel;

a reactor arranged inside the vessel and having a main portion surrounded by the light conducting liquid and disposed below a level of the light conducting liquid;

the reactor comprising:
an upper end arranged above the level of the light conducting liquid;
an inlet arranged above the level of the light conducting liquid and being open to the atmosphere; and
an outlet arranged above the level of the light conducting liquid, being open to the atmosphere, and being position at a level different from the inlet;
a reaction medium contained in the reactor and being guided in the reactor in a meandering manner;
at least one reactor element arranged in the reactor through which the reaction medium flows; and
said at least one reactor element comprising one of:
pipes connected at a bottom and being arranged vertically;
pipes connected at a bottom and being inclined at an angle relative to a vertical plane;
chambers connected at a bottom and being arranged vertically; and
chambers connected at a bottom and being inclined at an angle relative to a vertical plane;
wherein the reaction medium is introduced into the reactor and removed therefrom over an upper reaction medium surface and without pressure and freely to the atmosphere such that the flow of the reaction medium is stress-free for micro-organisms disposed therein, and
wherein the vessel is configured to allow light external to the vessel to pass into the light conducting liquid and the light conducting liquid conducts the light to the reactor.

2. The device of claim 1, wherein the photochemical process comprises at least one of:
a photocatalytic process:
a photosynthetic process;
a process of cultivation micro-organisms;
a process of producing micro-organisms;
a hydrocultivation process; and
a process for cultivating or producing phototrophic micro-organisms.

3. The device of claim 1, wherein the reactor is a bioreactor and the reaction medium is one of an aqueous solution and a suspension.

4. The device of claim 1, wherein one of:
the reactor comprises a transparent material; and
the reactor comprises a translucent material.

5. The device of claim 1, wherein one of:
said at least one reactor element comprises a transparent material; and
said at least one reactor element comprises a translucent material.

6. The device of claim 1, wherein said at least one reactor element comprises one of:
two or more reactor elements and a dividing wall connecting the two or more reactor elements;
two or more reactor elements arranged in a reactor panel;
two or more reactor elements, a dividing wall, and an overflow or interconnected opening arranged above a liquid level in the reactor; and
two or more reactor elements, a dividing wall, and an overflow or interconnected opening arranged above an upper end of the dividing wall.

7. The device of claim 1, further comprising one of:
reflectors arranged above the light-conducting liquid;
reflectors arranged above the vessel;
reflectors structured and arranged to guide light into the light-conducting liquid;
reflectors structured and arranged to guide light into the light-conducting liquid at right angle a light-conducting liquid surface; and
reflectors structured and arranged to guide sunlight into the light-conducting liquid at right angle a light-conducting liquid surface.

8. The device of claim 1, further comprising one of:
light collectors collecting light and guiding the light into the light-conducting liquid;
light filtering filters filtering light before it is guided into the light-conducting liquid; and
a guiding arrangement structured and arranged to guide light into the light-conducting liquid in a pulsed manner.

9. The device of claim 1, wherein the pipes of said at least one reactor element comprise one of:
foil tubes;
plastic tubes; and
tubes whose ends are connected with diversion devices.

10. The device of claim 1, wherein the chambers of said at least one reactor element comprise connected foils provided with parallel longitudinal welds and diversion devices.

11. The device of claim 1, wherein said at least one reactor element comprises one of:
a U-shaped pipe element connected with chambers formed by a longitudinal weld; and
a U-shaped pipe element having an elliptical cross section.

12. The device of claim 1, wherein said at least one reactor element comprises one of:
a U-shaped pipe element which comprises at least one borehole;
a U-shaped pipe element which comprises a plug-in pipe;
a U-shaped pipe element which comprises an integrated plug-in pipe;
a U-shaped pipe element which comprises micro-boreholes;
a U-shaped element which comprises at least one opening structured and arranged to allow introduction of an additive into the reaction medium; and
a U-shaped element which comprises at least one opening structured and arranged to allow removal of gaseous process products at a bottom side of the reactor.

13. The device of claim 1, wherein said at least one reactor element comprises first openings structured and arranged to cause a downward flow of the reaction medium in one part of the at least one reactor element and second openings structured and arranged to cause an upward flow of the reaction medium in another part of the at least one reactor element.

14. The device of claim 13, wherein the first openings are different in size than the second openings.

15. The device of claim 1, wherein the device is adapted to utilize at least one of:
an Archimedian screw;
a spiral of Da Vinci pump;
a mammoth pump;
a fluid transporter arranged inside the reactor; and
a fluid transporter arranged between the reactor and another reactor.

16. The device of claim 1, wherein the device is structured and arranged to be used in combination with one of:
a cover;
a dome;
a transparent material cover;
a translucent material cover; and
a cover arranged over a container or basin containing therein the device.

17. The device of claim 1, wherein the reactor is a biosolar reactor and further comprising:
the outlet being arranged at a level that is below the inlet.

18. A bioreactor for a photochemical process, the bioreactor comprising:
at least one reactor element arranged in a vessel;
said vessel comprising:
an open upper end and/or a side that is transparent or translucent to light; and
a light reflecting surface that reflects light;
a reaction medium inlet arranged at an upper end of the at least one reactor element and being open to the atmosphere;
a reaction medium outlet arranged at an upper end of the at least one reactor element, being open to the atmosphere, and being located below the reaction medium inlet;
a reaction medium contained in the at least one reactor element and being guided in the at least one reactor element in a meandering manner;
a light-conducting liquid arranged outside the at least one reactor element and inside the vessel;
a level of the light conducting liquid inside the vessel being below each of:
the upper end of the at least one reactor element;
the reaction medium inlet; and
the reaction medium outlet; and
said at least one reactor element comprising one of:
pipes connected at a bottom and being arranged vertically;
pipes connected at a bottom and being inclined at an angle relative to a vertical plane;
chambers connected at a bottom and being arranged vertically; and
chambers connected at a bottom and being inclined at an angle relative to a vertical plane;
wherein the reaction medium is introduced into the reactor and removed therefrom, respectively via the reaction medium inlet and the reaction medium outlet, over an upper reaction medium surface under atmosphere pressure such that the flow of the reaction medium is stress-free for micro-organisms disposed therein, and
wherein the vessel is configured to allow light external to the vessel to pass into the light conducting liquid and the light conducting liquid conducts the light reflected from the light reflecting surface to the at least one reactor element.

19. A bio-solar reactor comprising:
a device for guiding and/or filtering external light;
a vessel arranged to receive the external light via an open or transparent upper side;
a light-conducting medium arranged in the vessel and being configured to conduct the external light to plural reactor elements;
the plural reactor elements being connected in series and immersed in the light conducting medium;
an upper end of each reactor element being located above a level of the light conducting medium arranged inside the vessel;
a reaction medium inlet being open to the atmosphere and being located above the level of the light conducting medium;
a reaction medium outlet being open to the atmosphere, being located above the level of the light conducting liquid, and being position at a level below the reaction medium inlet; and
a reaction medium structured and arranged to move through each of the plural reactor elements in a meandering up and down manner;
each of the plural reactor elements further comprising one of:
pipes connected at a bottom and being arranged vertically;
pipes connected at a bottom and being inclined at an angle relative to a vertical plane;
chambers connected at a bottom and being arranged vertically; and
chambers connected at a bottom and being inclined at an angle relative to a vertical plane; and
wherein the reaction medium is respectively introduced and removed into and out of the reactor under atmosphere pressure such that the flow of the reaction medium within and between the plural reactor elements is stress-free for micro-organisms disposed therein.

* * * * *